United States Patent
Doerr

(10) Patent No.: US 8,965,495 B2
(45) Date of Patent: Feb. 24, 2015

(54) IMPLANTABLE ELECTRONIC THERAPY DEVICE

(75) Inventor: Thomas Doerr, Brelin (DE)

(73) Assignee: Biotronik Se & Co. KG, Berlin (DE)

( * ) Notice: Subject to any disclaimer, the term of this patent is extended or adjusted under 35 U.S.C. 154(b) by 877 days.

(21) Appl. No.: 13/195,560

(22) Filed: Aug. 1, 2011

(65) Prior Publication Data

US 2012/0053507 A1    Mar. 1, 2012

Related U.S. Application Data

(60) Provisional application No. 61/377,982, filed on Aug. 30, 2010.

(51) Int. Cl.
 *A61B 5/04* (2006.01)
 *A61N 1/362* (2006.01)

(52) U.S. Cl.
 CPC ................................ *A61N 1/3621* (2013.01)
 USPC ............... 600/518; 600/526; 607/6; 607/7; 607/14; 607/17; 607/62

(58) Field of Classification Search
 CPC ................................ A61B 5/02; A61B 8/02
 USPC ............... 607/6, 7, 14, 17, 62; 600/518, 526
 See application file for complete search history.

(56) References Cited

U.S. PATENT DOCUMENTS

| | | | |
|---|---|---|---|
| 6,873,870 B2 | 3/2005 | Ferek-Petric | |
| 6,993,385 B1 | 1/2006 | Routh | |
| 7,027,863 B1 | 4/2006 | Prutchi | |
| 7,519,422 B2 | 4/2009 | Lippert | |
| 2003/0083702 A1* | 5/2003 | Stadler et al. | 607/14 |
| 2004/0002741 A1 | 1/2004 | Weinberg | |
| 2006/0224201 A1 | 10/2006 | Hettrick | |
| 2009/0082825 A1* | 3/2009 | Arcot-Krishnamurthy et al. | 607/18 |

FOREIGN PATENT DOCUMENTS

| | | |
|---|---|---|
| FR | 2861996 | 5/2005 |
| WO | WO 0130436 | 5/2001 |

OTHER PUBLICATIONS

European Search Report dated Nov. 3, 2011 (6 pages).

* cited by examiner

*Primary Examiner* — Christopher D Koharski
*Assistant Examiner* — Natasha Patel
(74) *Attorney, Agent, or Firm* — ARC IP Law, PC; Joseph J Mayo

(57) ABSTRACT

An implantable electronic therapy device, having a therapy unit, a heart rate capturing unit, a contractility determination unit, and an evaluation and control unit. The therapy unit delivers an antitachycardiac therapy. The heart rate capturing unit determines a ventricular heart rate from an input signal, and the contractility determination unit generates from an input signal, a contraction signal reflecting a contractility of a ventricle. The evaluation and control unit is connected to the therapy unit, the heart rate capturing unit, and the contractility determination unit actuates the therapy unit to administer an antitachycardiac therapy when the heart rate capturing unit detects an increase in the heart rate above a specified threshold value and the contractility determination unit supplies a contraction signal which is not physiologically adequate for the increase in the heart rate.

13 Claims, 5 Drawing Sheets

IMPLANTABLE ELECTRONIC THERAPY DEVICE

This application claims the benefit of U.S. Provisional Patent Application 61/377,982, filed 30 Aug. 2010, the specification of which is hereby incorporated herein by reference.

BACKGROUND OF THE INVENTION

1. Field of the Invention

Embodiments of the invention relate to an implantable electronic therapy device.

2. Description of the Related Art

Such implantable electronic therapy devices are known, for example, as implantable cardioverters/defibrillators (ICDs), which trigger an antitachycardiac therapy such as a cardioversion shock or a defibrillation shock when the evaluation and control unit thereof detects specified criteria that indicate ventricular tachycardia (VT) or supraventricular tachycardia (SVT), notably an increase in the ventricular heart rate above a specified threshold value. For this purpose, heart rates are typically assigned to different frequency ranges, referred to as VT zones.

Antitachycardiac stimulators, in particular ICDs, known from the prior art employ a variety of rhythmological counters and ECG morphology criteria to control the antitachycardiac therapy in the VT zones in order to derive a decision on the therapy. Additionally, algorithms are employed, which take the combinations of such rhythm and morphology parameters into consideration.

Furthermore, it is known from U.S. Pat. No. 6,873,870 to include hemodynamic sensors, such as blood pressure and flow, in the evaluation of tachyarrhythmia according to the hemodynamic relevance.

BRIEF SUMMARY OF THE INVENTION

It is a feature of one or more embodiments of the invention to administer an antitachycardiac therapy in the case of VT or SVT only when hemodynamic relevance of the tachycardia is apparent. A goal of one or more embodiments the invention is in particular that, regardless of the origin of a fast ventricular rate, an antitachycardiac therapy, in particular a shock therapy, is administered only when the ventricular rate results in a hemodynamic impairment.

According to one or more embodiments of the invention, this object is achieved by an implantable electronic therapy device, comprising a therapy unit, a heart rate capturing unit, a contractility determination unit, and an evaluation and control unit, wherein:

the therapy unit is designed to deliver an antitachycardiac therapy, the heart rate capturing unit is designed to determine a ventricular heart rate from an input signal, the contractility determination unit is designed to generate, from an input signal, a contraction signal which reflects a contractility of a ventricle, and the evaluation and control unit is connected to the therapy unit, the heart rate capturing unit, and the contractility determination unit and designed to actuate the therapy unit to administer an antitachycardiac therapy when a) the heart rate capturing unit detects an increase in the heart rate above a specified threshold value
and
b) the contractility determination unit supplies a contraction signal which is not physiologically adequate for the increase in the heart rate.

According to one or more embodiments of the invention for example, a permanently implantable electronic therapy device for the antitachycardiac therapy of the heart comprises at least an apparatus for capturing a variable that corresponds to the contraction state and/or contraction dynamics (preferably: unipolar intracardiac impedance), and a unit for capturing the ventricular heart rate, and an evaluation and therapy control unit, wherein the evaluation and therapy control unit initiates an antitachycardiac therapy whenever the ventricular rate corresponds to VT and the captured contractility curve, relative to the increase in frequency, does not correspond to a curve to be physiologically expected.

Contrary to known implantable electronic therapy devices, the device according to one or more embodiments of the invention is therefore designed to administer an antitachycardiac therapy, in particular a shock therapy, only when the tachycardia can indeed result in hemodynamic impairment, by capturing not only the heart rate, but also contractility and including it in the therapy decision. The therapy decision is not dependent on the origin of the increased ventricular rate. In this way, a reduction of inadequate shocks or other therapies and an increase in the therapeutic efficiency of ICD systems or the like are possible. The device according to one or more embodiments of the invention requires only the right-ventricular electrode, which is generally present, or a comparable electrode, which is to say, there are no additional electrode or sensor requirements whatsoever.

One or more embodiments of the invention includes the observation that all known solutions have the disadvantage that either only the origin of the tachycardia or the duration of the tachycardia can be evaluated for the therapy decision. As a result, VTs are frequently treated too early with shock, without waiting for the opportunity of a spontaneous termination or without treating hemodynamically relevant SVTs (such as AV reentry), although shock therapy is a suitable therapy option here, despite the supraventricular origin of the arrhythmia.

The sensors described in U.S. Pat. No. 6,873,870 for the hemodynamic classification of the tachyarrhythmia into hemodynamically relevant and non-relevant tachyarrhythmias have the disadvantage that additional sensors are required for the pressure and/or flow. Additionally, U.S. Pat. No. 6,873,870 does not address the physiological relationship between the heart rate and contractility, and thereby ignores a very early indicator of an emerging hemodynamic relevance, because slower VTs initially cannot be diagnosed by classic hemodynamic parameters such as pressure and flow due to diverse compensation mechanisms. In contrast, reduced or unchanged contractility as one of the control variables for cardiac output can be used immediately as a discriminator.

One or more embodiments of the invention takes advantage of the physiological principle that each physiological increase in cardiac output is accompanied by an increase in the heart rate, with a simultaneous increase in the contraction force and contraction rate—this being contractility. In contrast, a non-physiological or pathological increase in the heart rate does not increase the contraction force and contraction rate or, as a compensatory measure, even reduces it. According to one or more embodiments of the invention, the therapy decision is therefore made contingent upon the examination of the physiological relationship between the increase in the heart rate and a parameter that corresponds to the contraction curve, which is to say for example, a plausibility check is conducted for the increase in the frequency.

A great advantage of this method compared to the known "true hemodynamic" measurements is that it only requires simple measurement, for example unipolar impedance measurement, in order to determine a "relative" parameter that corresponds to the contraction state. The fact that such measurement is adequate for regulating the implant has been sufficiently verified with the CLS (Closed Loop Stimulation:) principle. To this end, the lacking chronotropy is replaced with information of the contraction state by way of unipolar impedance measurement, and the rate adaptation of the pacemaker is controlled. The key is that this unipolar impedance measurement does not capture a truly hemodynamic variable, as is required, for example, in U.S. Pat. No. 6,873,870. This is also apparent from the current endeavors to capture hemodynamic characteristics by way of multipolar impedance measurements, because unipolar measurement is not sufficient.

Advantageous embodiments of the implantable electronic therapy device according to one or more embodiments of the invention are the following:

The implantable electronic therapy device according to one or more embodiments of the invention is an implantable cardioverter/defibrillator (ICD), a biventricular cardiac stimulator for resynchronization therapy (CRT-D) and/or an antitachycardiac cardiac pacemaker.

As an alternative or in addition, the implantable electronic therapy device may comprise a drug pump.

The implantable electronic therapy device may also be a stimulator for modulating the cardiac contractility.

The implantable electronic therapy device can also be a leadless ICD.

One embodiment of the implantable electronic therapy device is designed to discern the contractility information by way of continuous intracardiac impedance measurement at a ventricular electrode—according to the CLS principle. This can be done selectively in the right ventricle, in the left ventricle, bipolar or unipolar. The physiological basic principle of CLS pacemaker frequency adjustment is based on the fact that the contractility (inotropy) of the heart always increases with a physiological increase in the heart rate (chronotropy). If a patient suffers from sinoatrial node dysfunction and therefore chronotropic incompetence, the heart rate admittedly may not be adequately increased under physiological stress, but contractility will still rise. If it is possible to measure the contractility, the frequency adjustment by the cardiac pacemaker can then be controlled accordingly for these patients. For this purpose, a continuous unipolar impedance curve is recorded at the ventricular electrode tip after each ventricular excitation. This impedance signal is characterized by the varying conductivity of the surrounding myocardial tissue (lower conductivity) and the blood (higher conductivity). Upon contraction of the ventricle, the conductivity in the region of the electrode tip decreases, because blood volume is increasingly displaced by the contraction. In order to be able to derive a physiological controlled variable, the impedance curves are compared to reference impedance curves recorded under proven rest conditions, and an area difference is determined between the current and the reference impedance curves. The area difference is then the measure for the relative increased contraction dynamics for this one cardiac cycle and is used as a measure for adjusting the rate of the CLS pacemaker. The advantage of this method is the extremely robust and relatively simple measurement principle of unipolar impedance measurement, having a good signal-to-noise ratio, so that beat-by-beat measurements are possible, without the necessity of forming average values. The area difference of the impedance curves, however, is only a relative characteristic of the contraction dynamics and can neither be converted into an absolute value for the contractility or stroke volume, nor be evaluated over the long term. This means that the measurement signal is not long-term stable, so that the reference curves are continuously adjusted/updated.

One or more embodiments of the invention takes advantage of the same physiological approach in order to check, by way of a plausibility check, the increases in heart rates for the usually chronotropically competent ICD patients to determine whether they are the result of a physiological frequency adjustment or are rated as non-physiological, when no expected increase in contraction occurs with a frequency increase or takes an unexpected course. The measurement method used in the CLS principle is also sufficient for this.

According to an alternative variant, the implantable electronic therapy device is designed to discern the contractility information by way of transcardiac impedance measurement according to the HDS principle. To this end, a correlation is determined for the left-ventricular volume change during a ventricle contraction by way of 4-polar impedance measurement in that measurement current pulses are continuously applied in a bipolar fashion at the right- or left-ventricular electrode, and the additional voltages caused by the measurement currents are measured at the other electrode. Again, the change in conductivity resulting from the varying blood volume in the left ventricle is utilized to obtain a characteristic for the contraction dynamics. The advantage over the CLS measurement is the possibility to depict the left-ventricular contraction curve and thereby depict in particular the decompensation of the left ventricle. However, this measurement requires a bipolar left-ventricular electrode and the signal-to-noise ratio is worse than that of the CLS measurement.

This signal is also suited for examining, as claimed, the relationship between the increase in the heart rate and contraction dynamics.

According to a further alternative variant, the implantable electronic therapy device is designed to discern the contractility information by way of transthoracic impedance electrocardiography. In this method, which is sufficiently known, the change in the thoracic impedance during the heartbeat is evaluated. This signal as well contains information about the contraction dynamics at the time of the ventricular contraction (dZ/dt), which can be compared to the curve of the increase in the heart rate and classified. This method can be used for implants which, due to the design thereof, are not able to carry out a local impedance measurement at the ventricular probe or probes, this being in stimulators having no ventricular electrode.

According to another alternative variant, the implantable electronic therapy device is designed to discern the contractility information by way of intracardiac pressure measurement. If the implant has the possibility of an intracardiac, pulmonary arterial or aortic pressure measurement, the contraction parameters can also be derived from these hemodynamic measurement values and according to the invention be correlated with the increase in the heart rate. This approach, however, is only used to fully illustrate the method. When a pressure sensor is available, the hemodynamic relevance of arrhythmia can usually be derived directly.

The contractility signal preferably represents the contraction rate.

The evaluation and control unit is designed to initiate an antitachycardiac therapy whenever the ventricular rate corresponds to VT and the captured frequency increase is not or does not remain associated with positive inotropy, this meaning that the contractility does not rise together with the heart rate. Or in other words: The evaluation and control unit is designed to suppress the administration of an antitachycardiac therapy by the therapy unit when the heart rate capturing unit detects an increase in the heart rate above a specified threshold value and the contractility determination unit supplies a contraction signal which indicates that the corresponding contractility of the ventricle rises together with the heart rate.

The evaluation and control unit may always evaluate the criterion described above in combination with at least one further rhythmological or IEGM morphological criterion.

The evaluation and control unit may also be designed to assess a rise in the heart rate (frequency increase) as being physiological, this meaning that it does not require therapy, whenever a CLS signal likewise specifies a frequency increase within an appropriate tolerance, and in this case suppress the administration of an antitachycardiac therapy by the therapy unit. If, in contrast, the CLS signal remains considerably behind the observed frequency increase, the evaluation and control unit triggers an administration of an antitachycardiac therapy by the therapy unit. The CLS signal is derived in the known manner by comparing the intracardiac impedance curve when a patient is at rest to a current intracardiac impedance curve and reflects the particular hemodynamic need of a patient. A high hemodynamic need indicates a higher heart rate.

BRIEF DESCRIPTION OF THE DRAWINGS

Embodiments of the invention will now be described in more detail based on exemplary embodiments with reference to the figures. The figures show.

DETAILED DESCRIPTION OF THE INVENTION

A physiological frequency increase as a result of physical or mental stress always not only raises the heart rate, but also the contractility (positive inotropy).

When this characteristic or an auxiliary characteristic that corresponds to this characteristic is captured, a simple plausibility check can be used to decide whether a physiological increase in the ventricular heart rate is present, or whether an increase in the heart rate occurred due a pathological dysfunction of the stimulation and conduction.

In many cases, relatively slow ventricular tachycardias (VTs) can be hemodynamically tolerated for a certain period and do not require therapy during this time. Many of these slower VTs end due to spontaneous termination. However, if the contractility decreases during such VT, acute decompensation is safe to assume and an antitachycardiac therapy should be initiated.

Figure 1:
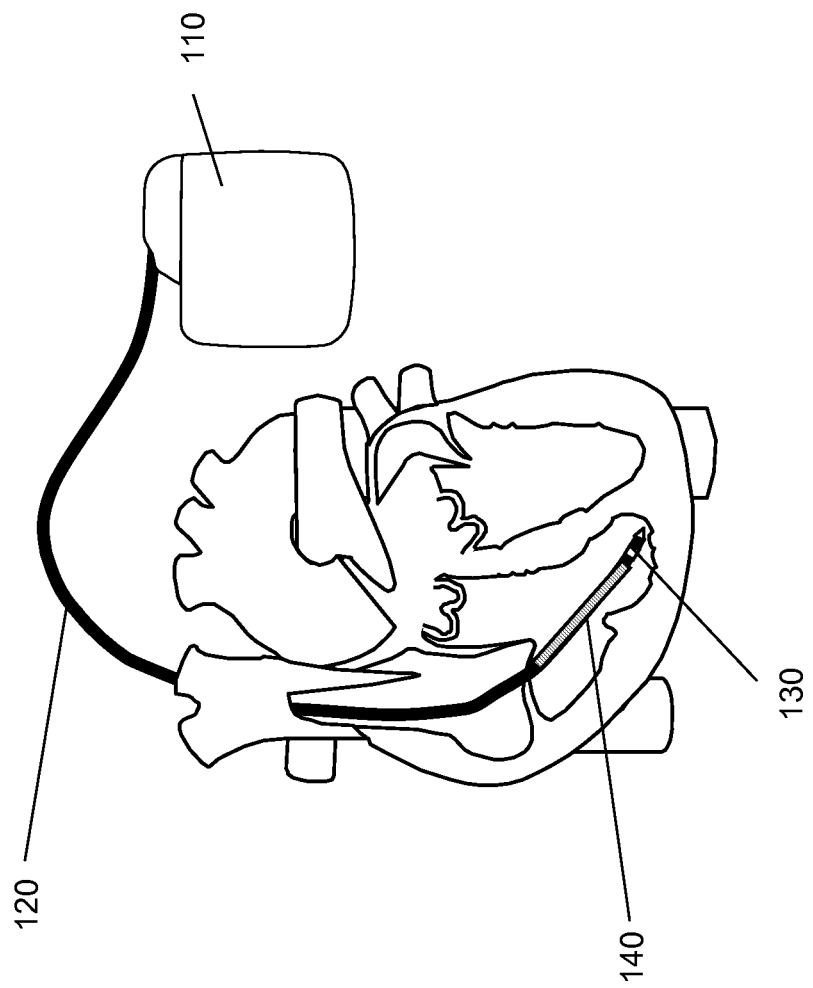
FIG. 1: a single-chamber ICD system.

FIG. 1 shows a single-chamber ICD system as an implementation example. A pulse generator 110 of the ICD is connected to a flexible implantable electrode lead 120. At the distal end thereof, the lead has a bipolar perception and stimulation pole 130. A distal 140, and optionally a proximal, shock coil are provided on the electrode lead 120 to deliver the defibrillation shock.

The impedance electrograms utilized for the claimed determination of the contractility information—and consequently of the contraction signal—are captured by feeding constant current pulses via the bipolar electrode pole 130 and the voltage required for feeding.

Figure 2A:
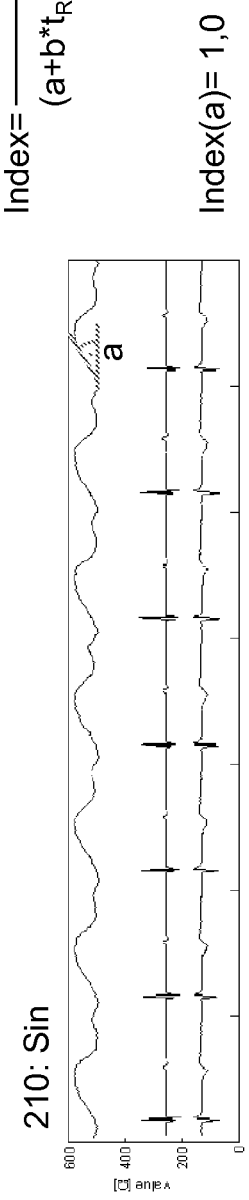
FIGS. 2A-C: illustrations of the contractility index for different heart conditions.
Figure 2B:
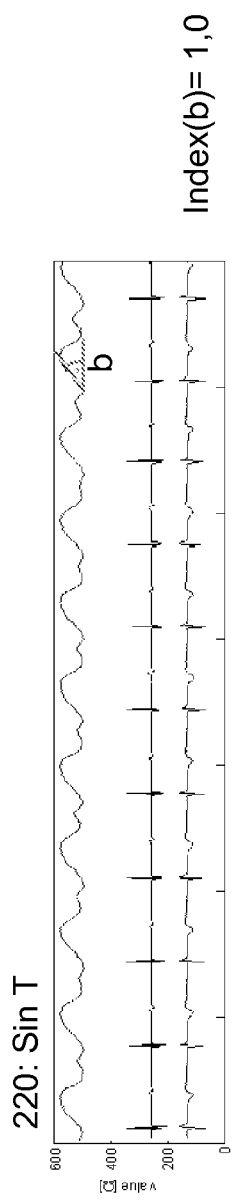
Figure 2C:
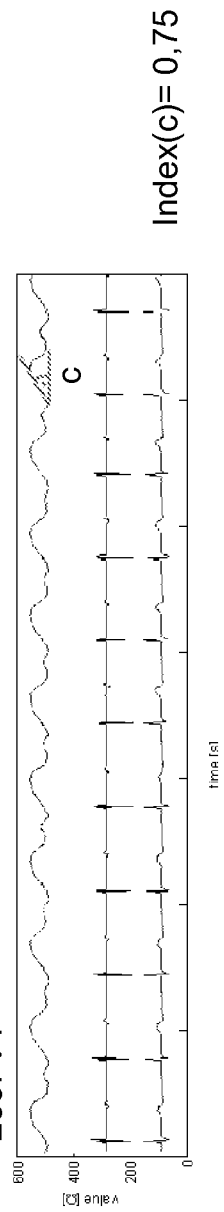

FIGS. 2A-C illustrates typical impedance cardiograms that have been recorded for various rhythm situations. The first graph 210 shows a sinus rhythm for a normal heart rate (top curve: impedance cardiogram, center: RV IEGM, bottom: LV IEGM). The increase in the impedance cardiogram (a) represents the contraction rate and is therefore a measure of the contractility. This value (dZ/dt) is used to form a corresponding frequency-weighted contractility index ("index"), which allows a standardized conclusion as to whether the contractility corresponds to a particular physiological heart rate. Here, the contractility index has been standardized to the value 1.0.

The second graph 220 illustrates a stress-induced frequency increase (dobutamine-induced). Here, dZ/dt (b) increases accordingly, so that the calculated contractility index likewise is approximately 1.0 and therefore shows a regular contractility increase with the frequency.

The third graph 230 shows ventricular tachycardia. Here, the contraction dynamics dZ/dt (c) reaches a lower value than in the case of the sinus tachycardia and therefore exhibits a smaller frequency-standardized contractility index of 0.75. As a result, here a delimitation between sinus tachycardia and VT is possible.

Figure 3:
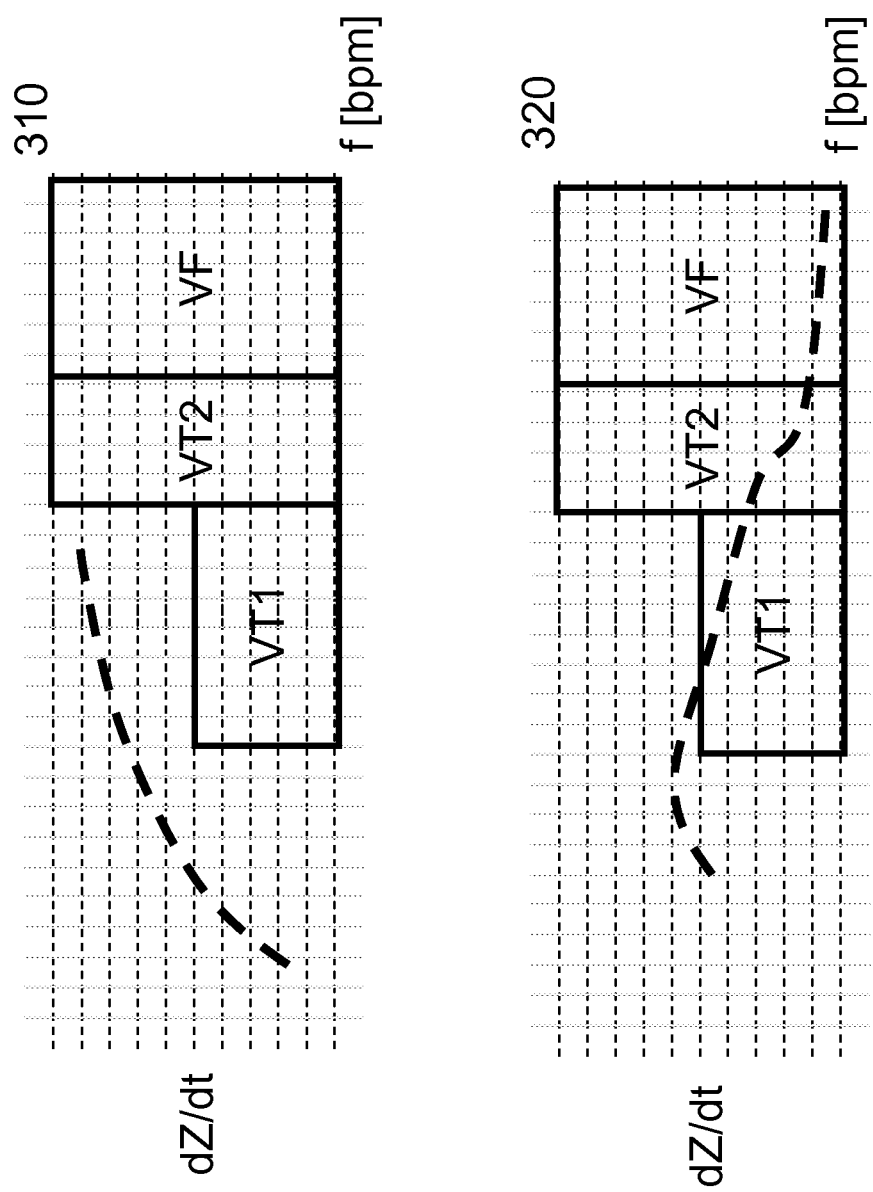
FIG. 3: examples of VT/SVT discrimination.

FIG. 3 shows an alternative method for the contractility-based VT/SVT discrimination. The top graph 310 shows the heart rate-dependent contractility curve (expressed in dZ/dt) for stress-induced sinus tachycardia. The curve runs above the zone marked with VT and requiring therapy (VT1). Starting at a critical rate, this being a rate that is not plausible for sinus tachycardia, the therapy requirement is expanded to the entire contractility spectrum (VT2/VF).

The bottom graph 320 shows the contractility curve to be expected for VT. At the start of the VT, it may still be in a range that does not require therapy, this being outside of VT1. As the frequency or duration of the VT increases, however, the contractility decreases into the therapeutic range.

Figure 4:
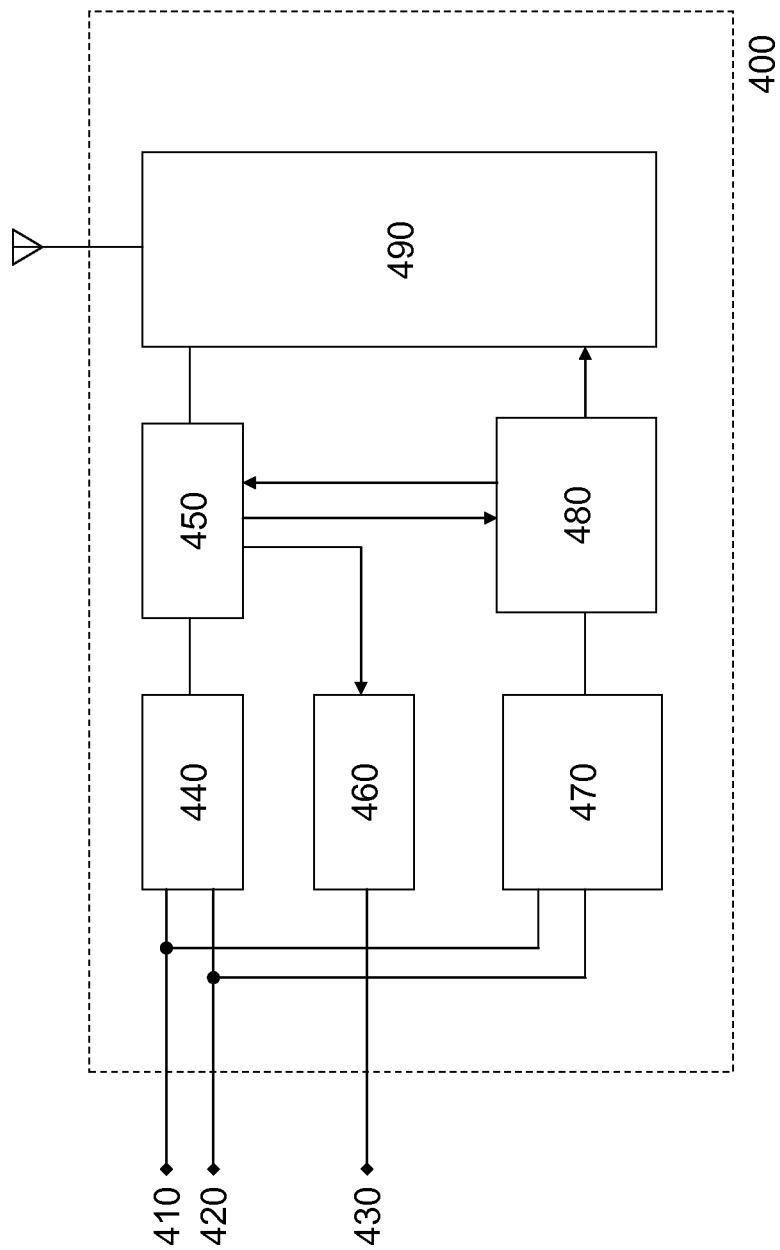
FIG. 4: a simplified block diagram of an ICD as that of FIG. 1.

FIG. 4 shows the block diagram of the ICD 400 from FIG. 1, which has been expanded according to one or more embodiments of the invention. It is connected to a bipolar stimulation and perception electrode 410, 420 and a shock coil 430.

An intracardiac electrocardiogram (IEGM) present at the bipolar perception electrode 420, 430, is initially ascertained in a conventional sensing stage 440 and classified in a subsequent rhythm evaluation unit 450. If tachyarrhythmia is detected, the rhythm evaluation unit 450 normally immediately initiates the delivery of a therapeutic shock by way of the therapy unit 460.

According to one or more embodiments of the invention, the ICD however has been expanded by an impedance-based contractility determination unit 470 and an additional control unit 480. The additional control unit 480 is formed at least when the rhythm evaluation unit 450 ascertains fast intervals (for example, 2 consecutive intervals within a VT zone). This control unit then activates the contractility determination unit 470 and determines the ventricular contractility index by way of impedance cardiography at the bipolar RV electrode. The additional control unit 480 then evaluates the result of this monitoring step. If the contractility index corresponds to a physiological frequency increase or exhibits a hemodynamically acceptable value in this frequency range, the antitachycardiac therapy is inhibited entirely, or at least a shock therapy. If the index shows a frequency-weighted contractility drop, the antitachycardiac therapy is approved and/or a shock therapy is forced.

The data of the rhythm classification and the determined contractility index are recorded in a unit 490 for storing diagnostic data and optionally made available telemetrically to the user.

Figure 5:
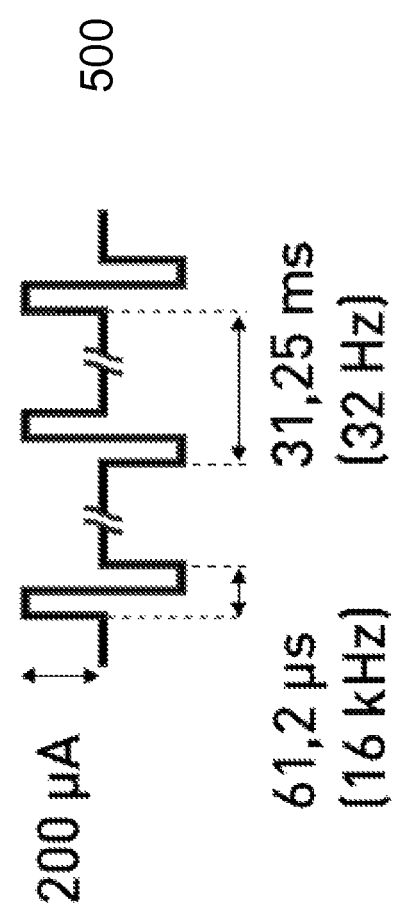
FIG. 5: current pulses suited for impedance measurement.

FIG. 5 shows typical current pulses 500 for the continuous intracardiac impedance measurement. These are sent continuously between the bipolar terminal of the right-ventricular electrode. The recording of the required voltage for feeding the constant current then produces the impedance electrocardiogram, which is subsequently used for detecting the rhythm and at the same time contains the information about the electrode integrity.

The current pulses illustrated here are already used for the intracardiac impedance measurement for CLS, for example, and are considered clinically safe.

The basic possibility of capturing a contractility variable by way of intracardiac impedance measurement is described, among other things, in U.S. Pat. No. 7,519,422.

It will be apparent to those skilled in the art that numerous modifications and variations of the described examples and embodiments are possible in light of the above teaching. The disclosed examples and embodiments are presented for purposes of illustration only. Therefore, it is the intent to cover all such modifications and alternate embodiments as may come within the true scope of this invention.

What is claimed is:

1. An implantable electronic therapy device, comprising
a therapy unit;
a heart rate capturing unit;
a contractility determination unit;
an evaluation and control unit;
wherein the therapy unit is configured to deliver an antitachycardiac therapy;
wherein the heart rate capturing unit is configured to determine a ventricular heart rate from an input signal;
wherein the contractility determination unit is configured to generate a contraction signal which reflects a contractility of a ventricle from said input signal;
wherein the evaluation and control unit is connected to the therapy unit, the heart rate capturing unit, and the contractility determination unit; and,
wherein the evaluation and control unit is configured to
derive a frequency-weighted contraction index from the contraction signal that reflects a ratio of the increase in the heart rate to an increase in the contractility,
conduct a plausibility check for an increase in frequency,
compare said frequency contraction index to standardized contraction index from a normal heart rate,
actuate the therapy unit to administer the antitachycardiac therapy when
the heart rate capturing unit detects an increase in a heart rate above a specified threshold value resulting in an increase in frequency,
and
the contractility determination unit supplies a contraction signal which is not physiologically adequate for the increase in the heart rate and the increase in frequency.

2. The implantable electronic therapy device according to claim 1, wherein the evaluation and control unit is further configured to
suppress deliverance of the antitachycardiac therapy by the therapy unit when
the heart rate capturing unit detects the increase in the heart rate above the specified threshold value
and
the contractility determination unit supplies the contraction signal which indicates that a corresponding contractility of the ventricle rises together with the heart rate.

3. The implantable electronic therapy device according to claim 1, wherein the contraction signal represents a contraction rate of the ventricle.

4. The implantable electronic therapy device according to claim 1, wherein the evaluation and control unit is configured to evaluate the frequency-weight contraction index in combination with at least one further rhythmological or intracardiac electrocardiogram morphological criterion.

5. The implantable electronic therapy device according to claim 1, wherein the evaluation and control unit comprises a rhythm evaluation unit, which is configured to capture the increase in the heart rate above the specified threshold value.

6. The implantable electronic therapy device according to claim 1, wherein the contractility determination unit is configured to determine the contraction signal through continuous intracardiac impedance measurement with a ventricular electrode.

7. The implantable electronic therapy device according to claim 1, wherein the contractility determination unit is configured to determine the contraction signal through transcardiac impedance measurement.

8. The implantable electronic therapy device according to claim 1, wherein the contractility determination unit is configured to determine the contraction signal through transthoracic impedance electrocardiography.

9. The implantable electronic therapy device according to claim 1, wherein the contractility determination unit is configured to determine the contraction signal through intracardiac pressure measurement.

10. The implantable electronic therapy device according to claim 1, wherein the evaluation and control unit is configured to suppress deliverance of an antitachycardiac therapy by the therapy unit when a comparison of an intracardiac impedance curve at rest to a current intracardiac impedance curve indicates an increase in the heart rate that corresponds to a current increase in heart rate, based on a specified tolerance.

11. The implantable electronic therapy device according to claim 1, wherein the implantable electronic therapy device is an implantable cardioverter/defibrillator, a biventricular cardiac stimulator for resynchronization therapy, and/or an antitachycardiac pacemaker.

12. The implantable electronic therapy device according to claim 1, wherein the implantable electronic therapy device further comprises a drug pump.

13. The implantable electronic therapy device according to claim 1, wherein the implantable electronic therapy device is a stimulator configured to modulate the cardiac contractility.

* * * * *